United States Patent [19]

Skriver et al.

[11] Patent Number: 5,459,052
[45] Date of Patent: Oct. 17, 1995

[54] METHOD OF PRODUCING IGF-1

[75] Inventors: Lars Skriver, Vedbæk; Kim R. Hejnæs, Lyngby; Henrik Dalbøge, Virum, all of Denmark

[73] Assignee: Novo Nordisk A/S, Bagsvaerd, Denmark

[21] Appl. No.: 87,477

[22] Filed: Jul. 2, 1993

Related U.S. Application Data

[63] Continuation of Ser. No. 746,827, Aug. 19, 1991, abandoned.

[30] Foreign Application Priority Data

Aug. 20, 1990 [DK] Denmark ........................ 1989/90
Oct. 16, 1990 [DK] Denmark ........................ 2497/90

[51] Int. Cl.$^6$ .......................... C12P 21/04; A61K 38/28; C07K 14/00; C12N 15/17
[52] U.S. Cl. .................. 435/71.2; 435/69.4; 435/320.1; 530/303; 530/399; 530/402; 530/412; 530/416; 530/417; 530/422; 530/427; 530/414; 436/161
[58] Field of Search ........................ 530/303, 399; 435/69.4, 69.8, 320.1, 71.2; 436/161

[56] References Cited

U.S. PATENT DOCUMENTS

| | | | |
|---|---|---|---|
| 4,933,434 | 6/1990 | Rudolph et al. | 530/405 |
| 4,961,969 | 10/1990 | Hershenson et al. | |
| 4,965,344 | 10/1990 | Hermann | 530/351 |
| 5,158,875 | 10/1992 | Miller et al. | |

FOREIGN PATENT DOCUMENTS

| | | |
|---|---|---|
| 0219874 | 10/1986 | European Pat. Off. |
| 0241022 | 4/1987 | European Pat. Off. |
| 0248362 | 5/1987 | European Pat. Off. |
| 0312358 | 4/1989 | European Pat. Off. |
| 2-234692 | 9/1990 | Japan. |
| 86/8012 | 10/1986 | South Africa. |
| WO87/02985 | 5/1987 | WIPO. |
| WO88/08003 | 10/1988 | WIPO. |
| WO88/10299 | 12/1988 | WIPO. |

OTHER PUBLICATIONS

Winkler et al., Bio/Technology, vol. 3, pp. 990–1000 (1985).
Wong et al., Gene, vol. 68, pp. 193–203 (1988).
Forsberg et al., J. Biochem., vol. 271, pp. 357–363 (1990).
Meng et al., J. of Chromatography, vol. 443, pp. 183–192 (1988).
Saito et al., J. Biochem., vol. 101, No. 1, pp. 123–134 (1987).
Light et al., Biochemistry, vol. 26, pp. 5556–5564 (1987).
Rudolph et al., Z. Physiol Chem., vol. 364, No. 7, pp. 813–820 (1983).
States et al., Nature, vol. 286 pp. 630–632 (1980).
Hager et al., Analytical Biochem., vol. 109, pp. 76–86 (1980).
Marston et al., Bio/Technology, vol. 2, pp. 800–804 (1984).
Forsberg et al. 1990 Biochem J. 271:357–363.
Marston 1986, The Purif. of Euk. poleypep. syn. in *E. coli*. Biochem. J. 240:1–12.
Sambrook et al 1988, Molecular Cloning: A Laboratory Manual, Cold Spr. Harbor Lab. Press, CSH, N.Y.
Peters, Gene, vol. 35, pp. 83–89 (1985).
Bornstein, P., et al., "Regulatory Elements in the First Intron Contribute to Transcriptional Control of the Human α1(I) Collagen Gene", *Proc. Natl. Acad. Sci. USA* 84:8869–8873 (Dec. 1987).
Weiss, M. J., et al., "Structure of the Human Liver/Bone/Kidney Alkaline Phosphatase Gene", *J. Biol. Chem.* 263(24):12002–12010 (Aug. 25, 1988).
Kieran, M., et al., "The DNA Binding Subunit of NF–κB Is Identical to Factor KBF1 and Homologous to the rel Oncogene Product", *Cell* 62:1007–1018 (Sep. 7, 1990).

*Primary Examiner*—Garnette D. Draper
*Assistant Examiner*—K. Cochrane Carlson
*Attorney, Agent, or Firm*—Steve T. Zelson; Cheryl H. Agris

[57] ABSTRACT

Ala-Glu-IGF-I is a novel compound which exerts IGF-I activity and is a precursor for the preparation of IGF-I. Ala-Glu-IGF-I may by converted to IGF-I by renaturation after recombinant production in *E. coli* under specified conditions and then cleaving Ala-Glu from the IGF-I.

20 Claims, 11 Drawing Sheets

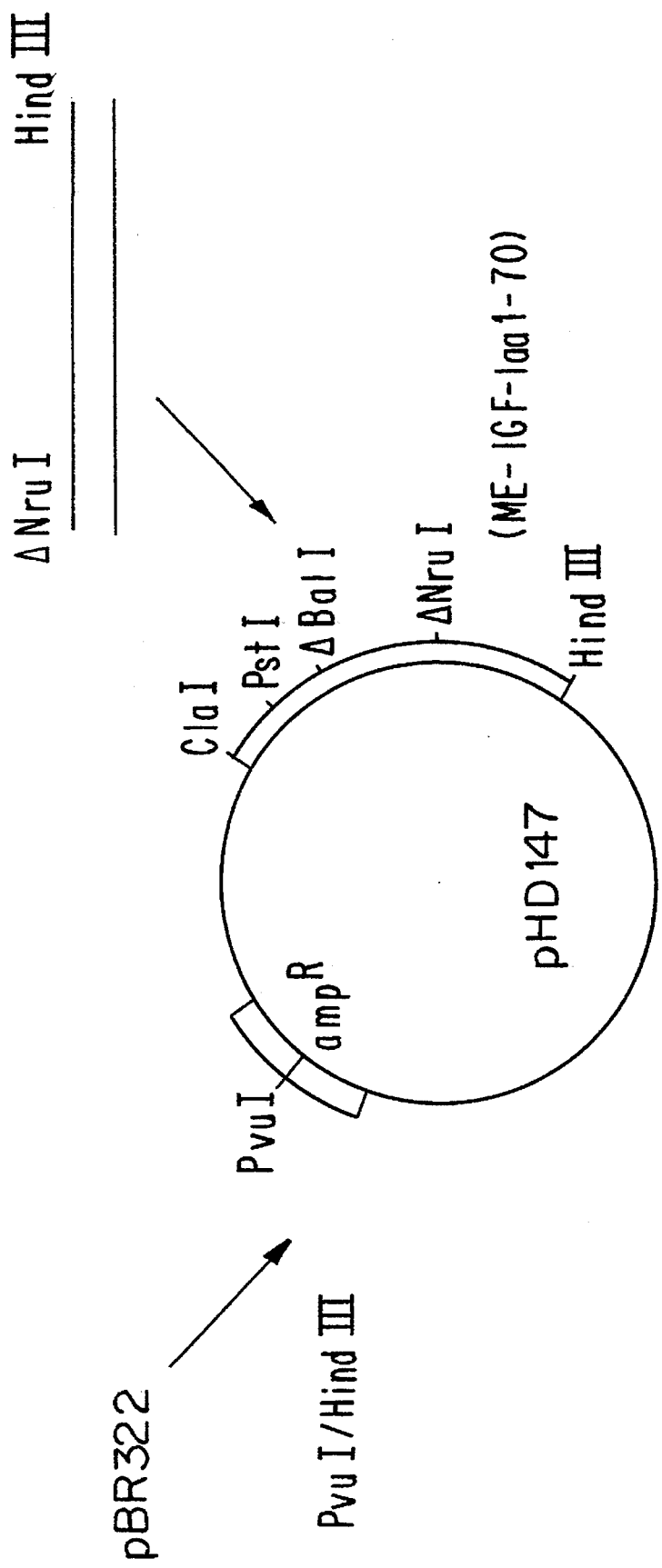
FIG. IC

FIG. 5 pHD 147

```
          30         40         50         60         70         80         90        100
TCATCGATGG AAGGTCCGGA AACTCTGTGC GGTGCTGAAC TGGTTGACGC TCTGCAGTTC GTTGCCGGTG ACCGTGGTTT
   C          B                                         P
   L          S                                         S
   A          P                                         T
   1          2                                         1

110        120        130        140        150        160        170        180
CTACTTCAAC AAGCCGACTG GTTACGGTTC TTCTTCTCGT CGTGCTCCCG AGACTGGTAT CGTTGACGAA TGCTGCTTCC
                                                                              B
                                                                              S
                                                                              N
                                                                              1

190        200        210        220        230        240        250
GCAGCTGCCGA CCTGGCTCGT CTGGAAATGT ACTGCGCC TCC GCTGAAGCCG GCTAAGAGCG CTTAGTAAGC TT
                                              N                              H
                                              A                              I
                                              E                              N
                                              1                              3
```

20 A

METHOD OF PRODUCING IGF-1

This application is a continuation application Ser. No. 07/746,827, filed Aug. 19, 1991, now abandoned.

The present invention relates to novel human insulin-like growth factor (IGF-1) having an amino terminal extension, a DNA sequence coding for IGF-1 having such an amino terminal extension, a recombinant plasmid comprising DNA coding for human IGF-1 having an amino terminal extension, a transformant microorganism containing such recombinant plasmid, a method for the renaturation of AlaGlu-IGF-1, a method for producing human IGF-1, and use of an amino terminal extended IGF-1 for the preparation of mature IGF-1. The invention is particularly suitable for use in large scale production of IGF-1.

BACKGROUND OF THE INVENTION

The insulin-like growth factors (IGFs) constitute a family of proteins having insulin-like and growth stimulating properties. The peptides have been purified from plasma, and their structure and chemical properties have been determined. The IGFs show close structural homology with proinsulin and elicit similar biological effects (Rinderknecht,E. and Humbel, R. E.: J. Biol. Chem., 253, 2769–2773 (1978), Zapf,J. et al.: Curr. Topics in Cell Reg., 19,257–309 (1981), Humbel,R. E.: Hormonal Proteins and Peptides, 12, AP 56–69 (1984), van Wyk,J. J.: Hormonal Proteins and Peptides, 12, AP 81–125 (1984)). Although being members of the same family of proteins, the two main forms of IGFs are rather different with respect to their chemical characteristics. IGF-1 is a basic peptide (pI 8.4) and shows a 43% homology with proinsulin (Rinderknecht, E. and Humbel,R. E.: J. Biol. Chem., 253, 2769–76 (1978). IGF-2 is an almost neutral peptide (pI 6.4) shows a 60% homology with IGF-1.

IGF-1 consists of 70 amino acids, the sequence of which has been determined by Rinderknecht,E. and Humbel,R. E.: J. Biol. Chem, 253, 2769–73 (1978). The physical-chemical parameters for IGF-1 have been studied extensively by several groups. The material used for these studies was primarily isolated from human plasma by a variety of conventional chromatographic methods. These include initial plasma fractionation and further precipitation of other proteins using acid ethanol extraction to remove binding proteins and other plasma proteins. The acidified IGF-1-enriched fraction was then subjected to cation exchange chromatography, and several steps of reversed phase and isoelectric focusing resulting in the collection of a few μg of purified IGF-1.

IGF-1 and to a lesser degree IGF-2 are found in plasma, but only a minor fraction is present in a free form. Specific binding proteins of high molecular weight having very high binding capacity for both IGFs act as carrier proteins or as modulators of IGF functions (Holly,J. M. P. and Wass,J. A. H.: J. Endocrinol, 122,611–618 (1989), Ooi,G. T., and Herrington,A. C.: J. Endocrinol., 118, 7–18 (1988)). The IGFs exert an insulin-like effect when present in high amounts although only to an extent of 1% of that of insulin. The somatic function of IGF-1 is formulated in the so-called "Somatomedin Hypothesis", suggesting that growth hormone released from the pituitary gland exerts its effect by stimulating IGF-1 release from the liver, which IGF-1 then mediates the somatogenic actions via binding to cell surface receptors in the target tissues (Salmon,W. D. Jr., and Daughaday,W. H.: J. Lab. Clin. Med., 49, 825–836, (1957). The principal local biological function of IGFs is as a potent mitogenic agent, although the effect is weaker than that measured e.g. for PDGF and FGF (Froesch et al.: Ann. Rev. Phyiol. 47, 443–467 (1985). Together with PDGF, IGF-1 shows synergistic biological effects (Kato et al.: Eur. J. Biochem., 129, 685–690 (1983), Stiles et al.: P.N.A.S., USA 76, 1279–1283 (1979)). The principal biological effects of IGF-1 are thus considered the function of propagating mitogenic responses, and of maintaining growth initiated by other factors under properly controlled conditions (O Keefe et al.: Mol. Cell. Endocrinol., 31, 167–186 (1983) .

The potency of IGF-1 as a mitogenic factor and the vast potential use thereof in e.g. wound healing and in nitrogen metabolism has encouraged a great number of biopharmaceutical companies to try to express IGF-1 in various organisms due to the small amount present in human plasma. Production of IGF-1 in yeast is favored by a very easy purification of a correctly folded polypeptide. However, there are certain significant drawbacks associated with the use of these expression systems. The yield of fermentation is low (few mg per liter of fermentation broth), and the risk of obtaining O-linked glycosylated forms of the molecule is significant (Gillerfors et al.: J. Biol. Chem., 264, 2748–53), (1989).

Expression in bacteria has until now been the most successful approach giving high yields of IGF-1 and IGF-2, but mostly in cell associated forms. It has also been tried to express IGF-1 fused to a stabilizing peptide. Such a peptide is normally of the same size as IGF-1 itself, and may have physico-chemical properties facilitating the purification of the resulting protein. The fusion protein is cleaved by either chemical or enzymatic cleavage, leaving the mature protein for isolation.

Extraction of the recombinant peptide (fusion peptide) is normally associated with a denaturating step followed by in vitro renaturation of the extracted IGF-1, resulting in the native conformation of IGF-1.

In the bacterial systems described so far, yields of from 1 to 1.5 grams per liter of fermentation broth have been described for biosynthetic expression of hGH. However, despite the high yield of expression only minor amounts of native IGF-1 is obtained because of uncontrolled formation of intra and inter molecular disulphide bridges. Therefore, bacterial expression of products containing such disulphide bridges has to be followed by in vitro renaturation during the later purification of the polypeptides which normally results in extensive losses of product.

The object of the present invention is primarily to overcome the problems described in the prior art with respect to producing IGF-1 in microorganisms in high yields.

As used in the present context, the expression "folding" is used to designate the process of establishing the tertiary structure of the protein, including the formation of the intramolecular disulphide bonds.

The expression "Renaturation" is used to designate the establishing of the native tertiary structure of the protein.

The expression "Denaturing" is used to designate the break-down of the tertiary structure of the molecules disrupting the disulphide bonds and/or uncoiling of the protein.

BRIEF DESCRIPTION OF THE INVENTION

The present invention relates to human IGF-1 having an amino terminal extension AlaGlu.

The amino terminal extension allows high expression of the extended IGF-1, easy renaturing or folding of the IGF-1 and easy and complete cleavage thereof using the enzyme Dipeptidyl Amino Peptidase (DAP-1, EC 3.4.14.1) to form the mature IGF-1.

Thus, it has surprisingly been found that the amino terminal extension AlaGlu overcomes the problems of the prior art. Furthermore, it is possible to purify the IGF-1 having correct N-terminus from the reaction mixture.

The AlaGlu-IGF-1 may be isolated as an intermediate in a purity >80%, preferably >90% and shows, when correctly folded, biological activity of IGF-1.

The present invention also relates to a DNA sequence coding for IGF-1 having the amino terminal extension AlaGlu. This short extension has been applied in the expression of IL-1β and hGH but has not been proposed for the expression of IGF-1.

The part of the DNA encoding IGF-1 may be cDNA, chromosomal DNA or entirely or partly synthetic DNA wherein any remainder of the DNA may be the corresponding cDNA or chromosomal DNA.

The nucleotide sequences used for the amino terminal extension and any synthetic part of the DNA encoding IGF-1 are preferably chosen to give the preferred codons for the chosen microorganism.

The expression of the amino terminal extended AlaGlu-IGF-1 results in an expression level of 1.5 g/liter (0.2 mM) AlaGlu-IGF-1 prior to extraction. This is approximately 4 to 5 times the specific expression obtained in systems applying longer fusion proteins. However, not all short-chain aminoterminal extentions give rise to high levels of expression. Expression of e.g. MetGluAlaGlu-IGF-1, (AlaGlu)$_6$-IGF-1, or IGF-1 itself all give rise to levels of expression 10 to 25 times below the level obtained expressing AlaGlu-IGF-1.

The DNA encoding AlaGlu-IGF-1 may be prepared from a cloned DNA sequence encoding the 70 amino acids of IGF-1 which is coupled with the following synthetically produced, dual-stranded DNA sequence in such a manner that the 3' end of the +strand is coupled to the +5' end of the gene encoding IGF-1 and the 5' end of the synthetic DNA strand is coupled to the 3' end of the gene by blunt end ligature

+5' CGATG GCT GAA

−3' TAC CGA CTT wherein the two first nucleotides of the +strand are a ClaI restriction site overhang and the following nucleotide sequence code for the amino acids MetAlaGlu.

According to a further aspect of the invention a gene being apt for industrial production, coding for an amino terminally extended IGF-1 ensuring the formation of a stable product, and furthermore to the secretion thereof into the periplasmic space or directly into the medium is provided.

According to a third aspect, the invention relates to a recombinant vector comprising DNA-coding for human IGF-1 having the amino terminal extension AlaGlu. The vector may be in the form of a plasmid comprising a promoter upstream the DNA coding for AlaGlu-IGF-1 and preferably comprises the temperature sensitive promoter λAPR coupled directly to the DNA coding for AlaGlu-IGF-1 and the OmpA signal sequence providing for the secretion of the AlaGlu-IGF-1 into the periplasmatic space or directly into the medium. This vector has been demonstrated to be apt for industrial production when inserted in E.Coli.

According to a fourth aspect the invention provides a transformed microorganism comprising said recombinant plasmid.

According to a fifth aspect, the invention relates to a method for the renaturation of AlaGlu-IGF-1 wherein AlaGlu-IGF-1, in a substantially denatured and reduced form, is folded in the presence of a mercapto reagent in its reduced form in a buffered aqueous solution. The renaturation takes place during the controlled change of the redox potential from ÷40 mV to +20 to +40 mV by dialysis against a buffer containing from 20–40% v/v ethanol over a period of up to 5 hours at a protein concentration of 0.1 to 0.6 mg/ml and a conductivity of 0.15 to 0.3 mS at ambient temperature and a pH of from 7.5 to 10.0 and finally acidifying the mixture to a pH below 5.

The mercapto reagent used in the method of the invention may be any mercapto reagent which does not form unwanted by-products, e.g. 2-mercaptoethanol, cysteine, cysteamin, preferably cysteine.

In accordance with the invention, the mercapto reagent is used in a concentration of from 0.01–10 mM, preferably a concentration of 0.1–5 mM and most preferred a concentration of 1 mM.

The buffered aqueous solution in which the folding or renaturation of the the invention is carried out is buffered to a pH in the interval from 8.0–10.0, preferably a pH of 9.0.

In some cases it is preferred to carry out the renaturation according to the invention in the presence of ethanol in an amount of up to 40%, preferably about 25%. Such addition increases the yield of the method, and the optional beneficial effect of ethanol is easily demonstrated by simple preliminary experiments.

According to a sixth aspect the invention relates to a process for producing IGF-1 comprising i) expression of an amino terminal extended IGF-1 in a microorganism transformed with an expression vector comprising an inducible promoter coupled directly to the DNA coding for human IGF-1 having an amino terminal extension and a signal sequence, providing for secretion of the expressed product, ii) extraction of amino terminal extended IGF-1 at pH>6.0 using high concentration of urea in the presence of a reducing agent and optionally a chelating agent, iii) subjection of the extract to chromatography on an anion exchange gel selected from the group consisting of DEAE, DE and FF-Q using the same buffer as in step ii) adjusted to 1.8–2.2 mS and pH 7.8–8.2, iv) renaturation of the isolated amino terminal extended IGF-1 changing the redox potential of the reaction mixture linearly from −40 mV to +20 to +40 mV by dialysis against a buffer containing from 20–40% v/v ethanol over a period of up to 5 hours keeping a protein concentration from 0.1 to 0.6 mg/ml and a conductivity of 0.15–0.3 mS, at ambient temperature and a pH of from 7.5 to 10.0 and finally acidifying the mixture to a pH below 5, v) cleaving the amino terminal extension using DAP-1, vi) isolation of the renatured authentic human IGF-1 from amino terminally extended IGF-1 using RP-HPLC and cation exchange chromatography, and vii) gel filtrating and lyophilizing the isolated human IGF-1.

The method of the invention may be carried out by expressing the amino terminally extended IGF-1 in a microorganism such as a grampositive bacterium or a gramnegative bacterium such as Esherichia, preferably E.Coli which is a very convenient host due to its industrial applicability.

According to the invention the promoter may be a temperature sensitive promoters such as $\lambda_{PR}$, $\lambda_{PL}$ or $\lambda_{PR}$, and the signal sequence may be LamB, OmpA or OmpF sequences in order to ensure a proper expression and secretion.

The AlaGlu-IGF-1 is expressed in a high level using the $\lambda_{PR}$ promoter directly coupled to the gene coding for Ala-Glu-IGF-1, and the OmpA signal sequence provides for secretion of the protein in a stable form.

The extraction of AlaGlu-IGF-1 is carried out under reducing and denaturing conditions using urea, reducing agents such as cysteine, 2-mercapto-ethanol or dithiothreitol and optionally chelating agent(s) such as EDTA in order to destroy the tertiary structure imposed on the AlaGlu-IGF-1 by the express ion system.

The extraction of the AlaGlu-IGF-1 in a totally denatured form is preferably carried out using a buffer containing 7M urea, 50 mM Cys at the isoelectric point (8.4) or pH 8.0.

The majority of contaminating proteins originating from E.coli are removed from the reduced and denatured AlaGlu-IGF-1 by anion exchange chromatography at the isoelectric point. This chromatography is preferably carried out at a conductivity of 2.0 mS at pH 8.0 and is preferably carried out as batch chromatography on DE-52 (Whatman) repeated on Fast Flow Q sepharose® (FF-Q®).

The reduced and denatured AlaGlu-IGF-1 is renatured into stable, AlaGlu-IGF-1 being correctly folded.

The renaturation process is carried out using dialysis under control of the redox potential, pH, the protein concentration and the temperature in the presence of chelating, denaturing and mercapto reagents, and in the presence of organic solvents.

The dialysis buffer is characterized by the presence of small amounts of a reducing agent (e.g. DDT, Cys, or 2-mercapto ethanol), a chelating agent, an organic compound to interact with hydrophobic bonding (such as tert-butanol, 2-propanol, ethanol, methanol), and finally a buffer substance to maintain a well defined pH interval, typically 8.8 to 9.0. In one embodiment, the following buffer composition was used: 50 mMtris-HCl, 1 mM Cys, 2 mM EDTA and 25% ethanol at pH 9.5.

The renaturation is preferably carried out by changing the redox potential linearly from about −30 mV to between +25 and 30 mV over a period of 3 hours. The redox electrodes are calibrated using a hydroquinone solution having a well defined redox potential of 463 mV.

It is preferred to carry out the renaturation at a conductivity of 0.2 mS concentration of proteins of 0.1 to 0.4 mg/ml and a pH from 8.5 til 9.5 especially preferred a pH of 8.5 to 9.0 as measured in the buffer before addition of ethanol in a concentration of from 20 to 40% (v/v) and at a temperature of from 20° til 22° C.

According to a most preferred aspect, the renaturation of AlaGlu-IGF-1 is carried out passing the polypeptide through a hollow fiber device (Nephross Presto,H.F., Organon Teknika) at a flow rate from 25 to 250 ml/min, preferably about 100 ml/min while changing the redox potential, until the process is terminated by adding 5M acetic acid to a pH below 5, preferably pH 4.0.

The resulting solution is then concentrated by cation exchange chromatography in the presence of organic solvents before cleaving off the amino terminal extension. The cation exchange is preferably carried out using a strong ion exchange material such as FF-S® or FF-SP® in the presence of 10–40% alcohol such as methanol, ethanol, a propanol or a butanol, preferably 25% ethanol and using a pH gradient between 3.5 and 7.5.

The cleavage of renatured AlaGlu-IGF-1 is preferably carried out using the exopeptidase (DAP-1) giving a quick and efficient cleavage of the IGF-1 precursor. The exopeptidase is preferably used in a concentration of 0.08 units DAP-1 per mg protein in the presence of NaCl adjusting the protein concentration to approximately 1 mg/ml in a 40 mM acetate buffer at pH 4.0 and 37° C.

Reversed phase HPLC purification of IGF-1 after cleavage using DAP-1 may be performed on a RP18-column either of a commercial type (Lichrosorb) or custom made C18 silanoyl RP18 column. Preferably a 15 μm Novo Nordisk A/S silanoyl-RP18 column eluted at pH 3.0 in a 0.1M Na-phosphate buffer using a 30–50% ethanol linear gradient is used.

Any IGF-1 not being correctly folded will be removed by reversed phase chromatography on a RP18-column either of a commercial type, e.g. Lichrosorb, or custom made $C_{18}$ silanoyl RP18 column using ethanol os the mobile phase and remaining AlaGlu-IGF-1 will be removed using cation exhange chromatography starting at acid conditions and applying a pH-gradient from pH 4.0 to pH 7.0 using the same buffer system as in the above cation exchange procedure.

The purified IGF-1 is then subjected to lyophilization and gelfiltration. The lyophilized IGF-1 is taken up in 7 M urea, and applied to a G50F GPC Sephadex® column equilibrated in 0.1M acetic acid at 4° C. The purified material is stored at 4° C.

Finally, the highly purified IGF-1 is subjected to dialysis and gelfiltration and lyophilization to form a lyophilized, chemically stable powder.

Yet another aspect of the invention is a partial purification of the amino terminally extended IGF-1 in a fully denatured and reduced form.

A selective separation of amino terminally extended IGF-1 from IGF-1 having the correct amino terminus and amino acid sequence is obtained using cation chromatography, after cleaving the aminoterminal extension using DAP-1 in accordance with the principle described by Dalboege, H. et al. FEBS Lett. 246 (1,2) 89–93, 1989.

The removal of incorrectly renatured (folded) forms of IGF-1 by reverse phase HPLC is obtained using an octadecyl-dimethyl-silyl-substituted silica matrix comprising 15μ spherical particles having 300 Å pore diameters.

The characterization of the renatured IGF-1 with respect to the correct positioning of the disulphide bridges was carried out using two enzymatic cleavages followed by peptide mapping and sequence analyses.

The process of the invention has the further advantage that it can be upscaled directly.

A valuable aspect of the invention is the extraction procedure giving very high yield (close to 100%) of AlaGlu-IGF-1. The amino terminally extended IGF-1 is then purified using a specific FF-Q® anion exchange chromatography step at pI conditions under which AlaGlu-IGF-1 is not bound to the resin, whereas proteins originating from E.Coli and a polypeptide exibiting physical-chemical characteristics similar to that of AlaGlu-IGF-1, are removed under these specific conditions. Another valuable aspect of the invention is the specific renaturation step. This step is characterized by the continuous control of redox potential, ion strength and temperature during the renaturation of AlaGlu-IGF-1.

It has been found that modifications of the presequence drastically changes the conditions for renaturation.

The invention further provides a new concept for the cleavage of an N-terminal extension of IGF-1 using DAP-I (EC 3.4.14.1.), and application of a mild denaturation of the correctly folded IGF-1 prior to the final gel permeation chromatography step.

Thus, the invention apply a series of unique conditions which taken together improves the quality of the product and yield of the down-stream process following the fermentation.

The process may be scaled up to amounts in the order of grams per run, and a high degree of purification, illustrated by the low content of proteins originating from E.Coli (<1 ppm), is obtained.

The product is shown to have an amino acid composition, amino acid sequence, disulphide bridging and peptide mapping identical to those seen for IGF-1 purified from human plasma. The product is further characterized by showing one single band after SDS-polyacrylamide gel electrophoresis, and on native gels. Finally the product is characterized to be more than 95% pure by analytical reversed phase HPLC and GPC.

Furthermore, the invention relates to the use of IGF-1 having the amino terminal extension AlaGlu for the preparation of mature IGF-1.

The biological activity of the product of the method of the invention is equal to that of native IGF-1 purified from plasma. The product may e.g. be used for the treatment of wounds during wound healing, healing of fractured bones, metabolic disorders, and Diabetes type II (NIDDM). The IGF-1 may be formulated in any manner known per se for the formulation of pharmaceutical preparations or administration forms comprising IGF-1.

BRIEF DESCRIPTION OF THE DRAWINGS

The invention is described more in detail below with reference to the drawings in which FIG. 5 shows the DNA sequence of pHD 147 encoding IGF-1.

The invention is further explained with reference to the specific Examples.

EXPERIMENTAL PART EXAMPLES

Example 1

Construction of IGF-1 gene.

Figure 1A:
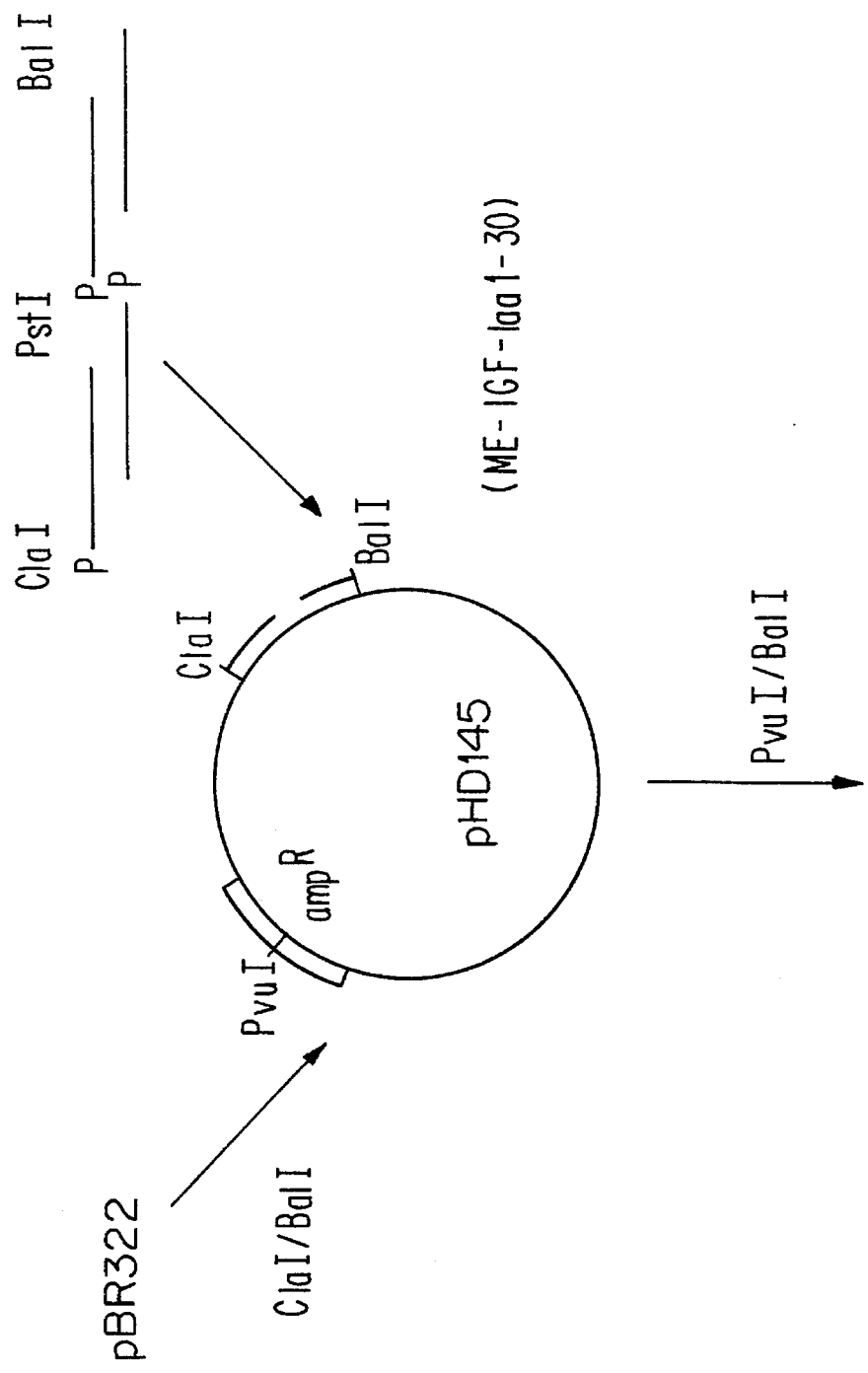
FIG. 1 shows the cloning strategy of a vector coding for Ala-Glu-IGF-1.
Figure 1B:
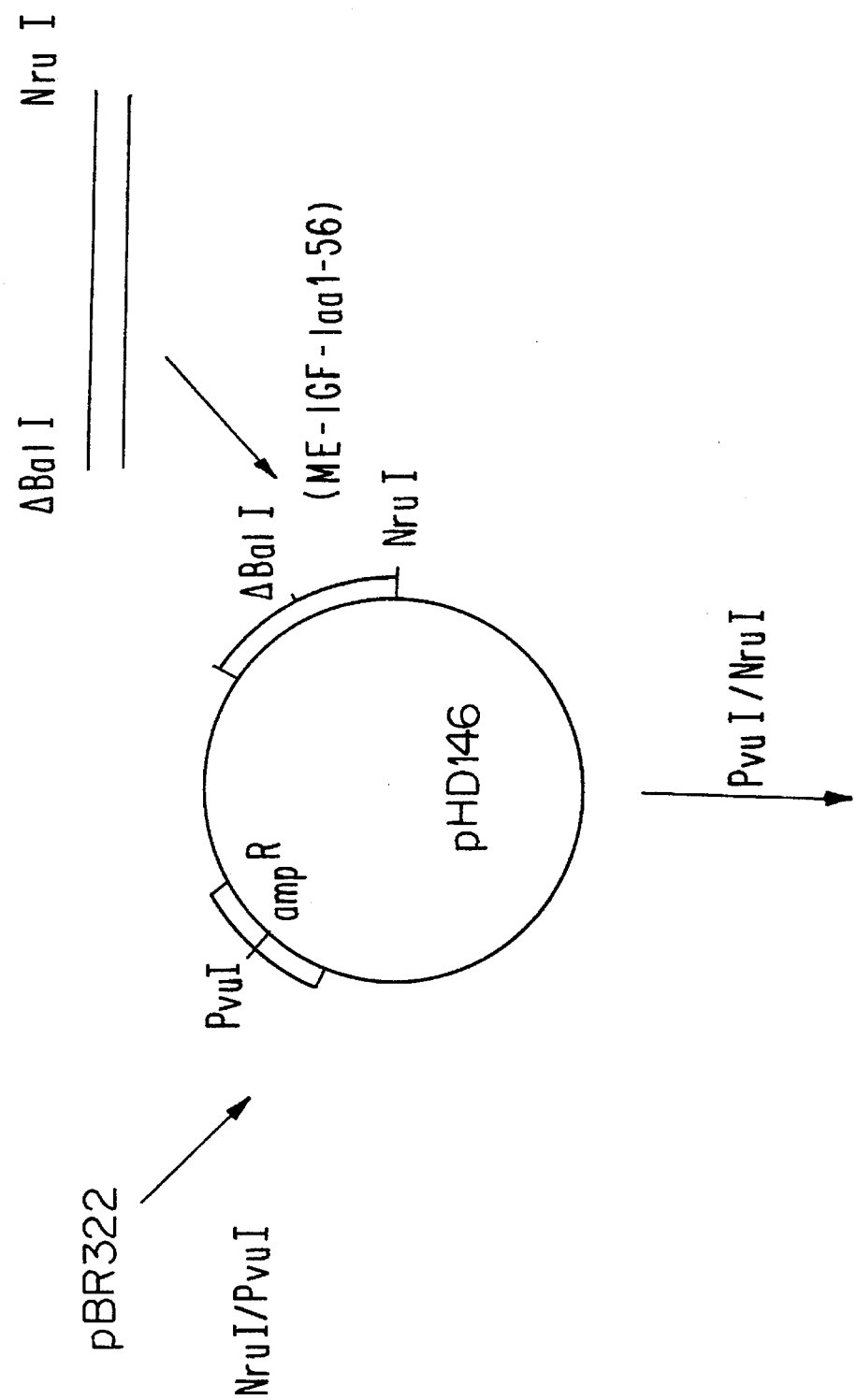

A synthetic gene for MetGlu-IGF-1 was constructed on basis of the published amino acid sequence (Jansen et al. 1983). Using optimum E.Coli codons, the gene was constructed from synthetic fragments which, following annealing and purification on gel, was cloned stepwise between unique restriction sites in appropriate cloning vectors (FIG. 1).

Construction of plasmid pHD145 (plasmid encoding aa 1–30 of MetGlu-IGF-1):

Preparation of linker: 0.4 µg of each of the linkers upper a, lower a and upper b were kinated separately by adding 1 µl 10×kinase buffer, 1 µl 10 mM ATP, 1 µl T4 PNK (10 units), 6 µl H$_2$O. Incubation at 37° C. for 30 min. The mixture was then heated to 65° C. for 10 min.

10 µl kinased upper a and 10 µl kinated lower a were annealed by heating to 100° C. for 3 rain and cooling on ice.

10 µl kinased upper b was annealed to 0.4 µg lower b (not kinated) by heating to 100° C. for 3 min. and cooling on ice.

Ligation of linker: 20 µl a, 11 µl b, 4 µl 10×ligase mix, 1 µl ligase (0.5 unit), 4 µl H$_2$O were mixed and incubated at 15° C. for 2 hours. The mixture was run on a 1.8 % low melting agarose gel. A fragment of 100 bp was isolated and purified using elutip. After precipitation, the fragment was dissolved in 50 µl H$_2$O. 2 µl were taken out and checked on 2% agarose gel.

Preparation of plasmid:

The above purified linker was then cloned in pBR322 digested with ClaI/BalI. In order to facilitate the digestion of pBR322 with BalI it is necessary to culture this plasmid in a not methylating strain of E.coli. Hence, pBR322 was transformed into the bacteria strain E.coli GCl17, which is DCM minus and DAM minus. 10 µl pBR322 (from GCl17) was digested using 5 U ClaI/3 U BalI in a low salt buffer in a final volume of 100 µl. The incubation was at 37° C. for 2 days and nights.

A DNA fragnent of about 1900 bp (plasmid fragment) was purified on 0.7% low melting agarose gel. After elution using elutip, the DNA was dissolved in 40 µl H$_2$O.1 µl aliquot was checked on gel.

Ligation of pHD145:

The following ligations were set up:

|  | A | B | C |
| --- | --- | --- | --- |
| 100bp DNA linker a + b | 3 µl | 3 µl | 3 µl |
| pBR322 ClaI/BalI | 1 µl | 0.05 µl | 0.05 µl |
| T4 DNA ligase | 0.05 unit (1 µl) | 0.05 unit (1 µl) | 1 unit (1 µl) |
| 10 × lig mix | 1 µl | 1 µl | 1 µl |
| H$_2$O | 4 µl | 4 µl | 4 µl |
|  | Control A | Control B | Control C |
| 100 bp DNA linker | 0 | 0 | 0 |
| pBR32 ClaI/BalI | 1 µl | 0.05 µl | 0.05 µl |
| T4 DNA ligase | 0.05 unit | 0.05 unit | 1 unit |
| 10 × lig mix | 1 µl | 1 µl | 1 µl |
| H$_2$O | 7 µl | 7 µl | 7 µl |

All the ligations were incubated at 15° C. for 3 hours, transformed into MC1061, plated on LB+ampicillin (LBA) agar plates on nitrocellulose filter and incubated at 37° C. over night. The reading of the plates on the next day showed that there was a greater number of colonies on the control plates than on the plates to which was added 100 bp fragment. Hence, it was decided to screen for any positive transformants by DNA hybridization.

Colony hybridization:

A copy of each filter was replicated onto a fresh nitrocellulose filter, both filters were transferred to LBA plates and incubated at 37° C. over night. The bacteria on one of the filters were lysated for 2 min. in 0.5M NaOH, 1.5M NaCl followed by washing in 0.5M Tris, pH 8, 1.5 NaCl for 2 min., and 2×SSC for 2 min. The filters were dried, baked for 1 hour at 80° C., and hybridized to a probe.

Preparation of probe:

1 µl (0.4 µg) IGF-1 upper a, 1 µl (0.4 µg) IGF-1 upper b, 100 µCi γATP (10 µl ), 2 µl 10×kinase buffer, 1 µl (5 unit) PNK, H₂O ad 20 µl were mixed and incubated at 37° C. for 30 min. The baked filters were, after prehybridization at 65° C., added to the above probe in a 50 ml hybridization volume. The hybridization was carried out at 60° C. over night. The filters were washed in 2×SSC followed by wash in 0.1×SSC, 50° C., dried and placed on a film.

15 positive colonies were cultured in LBA at 37° C. over night. Analysis of miniprep. DNA using the enzymes ClaI/PvuII showed, after run on 1.5 % agarose gel, that all clones except clone 11 comprised the expected DNA fragment of 745 bp. In order to further analyze some of the clones, i.a. for presence of the BalI/ClaI fragment of about 100 bp, the clones 1, 2, 3, and 4 were transformed into E.coli GC117 and plated on LBA agar plates. A single colony was chosen from each of the four plates and used for propagating maxiprep DNA. Digestion of the four plasmid preparations showed that the constructions 1, 2, and 3 had the expected restriction sites, but that clone 4 lacked the BalI site.

Construction of pHD146 (plasmid having sequence coding for aa 1-56 of MetGlu-IGF-1):

100 µl maxiprep DNA from pHD145–1, 2, and -3, respectively, was digested with 20 unit BalI over night at 37° C. in low salt. After checking digestion on agarose gel, the DNA was digested with 20 unit PvuI over night at 37° C. in high salt. After the digestion, the DNA was fractionated on 0.7% prep. agarose gel. A DNA fragment of 750 bp was isolated from each clone, elutipped, precipitated and dissolved in 20 µl H₂O. 0.4 µg linker C+D upper+lower were annealed in 20 µl H₂O at boiling for 5 min. and cooled on ice. The annealed linker was then purified on 2.5% prep. gel, a band of 70 bp was isolated, eluted from the gel using elutip, precipitated and dissolved in 20 µl H₂O.

The purified linker was kinated by adding 1 µl 10×kinase buffer, 1 µl 10 mM ATP, 5 unit PNK, and H₂O to 10 µl followed by incubation at 37° C. for 1 hour.

20 µl pBR322 DNA were digested with 50 unit PvuI/50 unit NruI in high salt in a final volume of 100 µl. After digestion, the DNA was fractionated on a gel, and a fragment of about 2800 bp was isolated, purified on elutip, precipitated and dissolved in 20 µl H₂O.

The below ligations A, B, control C, and control D were set up with fragments isolated from pHD145–1, -2, and -3, respectively.

|  | A | B | Control C | Control D |
|---|---|---|---|---|
| 10 × lig mix | 2 µl | 2 µl | 2 µl | 2 µl |
| 2800 bp fragment | 0.5 µl | 0.5 µl | 0.5 µl | 0,5 µl |
| 750 bp fragment | 0.5 µl | 0.5 µl | 0.5 µl | 0 |
| 70 bp kinated linker c + d | 10 µl | 1 µl | 0 | 0 |
| H₂O | 6 µl | 15 µl | 16 µl | 16.5 µl |
| T4 DNA ligase 0.1 U/µl | 0.1 U | 0.1 U | 0.1 U | 0.1 U |

The above ligations were incubated at 15° C. over night, transformed into MC1061 and plated out on LBA plates on nitrocellulose filter. Five plates were used per ligation. After incubation over night at 37° C., all the plates were replicated and treated as described above under construction of pHD145. 1 µl (0.4 µg) upper c and 1 µl (0.4 µg) upper d labelled as described for pHD145 was used as probe.

Hybridization and washing conditions were as described above. After development of film, 24 positive colonies were chosen and propagated to miniprep DNA in LBA medium. The DNA was analyzed by digestion with NruI/EcoRI and run on 1.5% agarose gel. The clones 3, 4, 5, 8, 13, 16, 18, 19, 20, and 21 looked right. Clone 3 and 13 were selected for closer analysis and propagated for maxiprep DNA.

The 24 isolated clones were isolated from the following ligations:

| Ligation reaction | 750 bp pHD145- | Plate no. |
|---|---|---|
| 1 | A | 1 | b |
| 2,3,4,5,6 | B | 1 | a |
| 7,8 | B | 1 | c |
| 9 | A | 2 | b |
| 10 | A | 2 | c |
| 11,12,13,14 | B | 2 | c |
| 15,16 | B | 2 | e |
| 17 | A | 3 | c |
| 18 | A | 3 | d |
| 19,20,21 | B | 3 | c |
| 22,23,24 | B | 3 | d |

Cloning of pHD147 (plasmid having the sequence encoding aa 1-70 of MetGlu-IGF-1 (FIG. 1)):

50 µl maxiprep DNA from pHD146-3 and pHD146-13, respectively, was digested with 20 unit NruI and 15 unit PvuI in 55 µl final volume (medium salt). 10 µl pBR322 plasmid DNA was digested with 15 unit PvuI and 36 unit HindIII in 55 µl final volume (medium salt). Both digestions were fractionated on 0.8% low melting agarose gel. From the clones pHD146-3 and -13 a 800 bp fragment was isolated, elutipped, precipitated and dissolved in 50 µl H₂O. From pBR322 a 3500 bp fragment was isolated, elutipped, precipitated and dissolved in 50 µl H₂O.

Linker IGF-1 e was annealed and purified on 2.5% prep. agarose gel as described for the previous linkers.

A 50 bp fragment was isolated and dissolved in 50 µl H₂O.

All the above fragments were checked on agarose gel.

Ligation of pHD147:

|  | A | B |
|---|---|---|
| pBR322 3500 bp fragment | 1.5 µl | 1.5 µl |
| pHD146-3 800 bp fragment | 10 µl | 10 µl |
| 50 bp linker e | 2 µl | 0 |
| 10 × lig mix | 1.5 µl | 1.5 µl |
| T4 DNA ligase 1 U/µl | 1 unit | 1 unit |

The ligation was carried out using the 800 bp fragment from pHD146–3 as well as from pHD146-13. The ligations were incubated for 3 hours at 15° C., transformed into MC1061, and plated on LBA plates. The filters were replicated, washed and hybridized as described above. 2 µl IGF-1 e lower DNA was used as probe. 6 positive clones were selected from filters where DNA from clones pHD146-3 and pHD146-13, respectively was used. These clones were called pHD-1->6 (pHD146-3+linker e) and pHD147-7->12 (pHD146-13 + linker e). Analysis of miniprep. DNA from the 12 clones using the restriction enzymes EcoRI/HindIII showed that all clones had the expected fragment. The clones 1 and 2, 7 and 8 were chosen for a closer analysis with digestion with the restriction enzymes HindIII/ClaI, PvuII/BamHI, PstI/BamHI. It appeared that all the clones had the expected restriction pattern. The clones pHD148-1 and pHD147-7 were propagated to maxiprep. DNA. Simultaneously miniprep. DNA was isolated from the clones 1, 2, 7, and 8 digested with the restriction enzymes EcoRI, HindIII, and a 220 bp fragment was isolated, cloned in M13, MP18 and MP19 and subjected to sequence analysis. The DNA sequence analysis showed that the clones comprised the expected DNA sequence.

Example 2

Cytoplasmic production of MetGlu-IGF-1

The plasmid pHD148-1 was digested with HindIII in the presense of Klenow DNA polymerase and dNTP, phenol extracted, precipitated and digested with ClaI. The excised gene was introduced into the expression plasmid pHD86SP13 (Dalboge et al. 1987), Biotechnol. 5, 161 ff), and introduced into E.coli MC1061.

Extracts from bacteria containing the expression plasmid were analyzed in a IGF-1 specific RIA and by Western blot. Non of the analyzed clones were found to express detectable quantities of IGF-1. In E.coli small cytoplasmic foreign polypeptides (less than 90–100 amino acids) have a tendency to be breaked down as they are recognized as incorrectly synthesized proteins. Transport of such proteins to the periplasma where the proteolytic activity is qualitatively different from the activity in the cytoplasm may stabilize these polypeptides.

Example 3

Periplasmic production of AlaGlu-IGF-1.

The signal peptide used was from OmpA of E.coli. In the natural OmpA precursor the signal peptide is processed between two alanine residues. To maintain this processing site the MetGlu-IGF- 1 gene was altered by in vitro mutagenesis to AlaGlu-IGF-1. This gene was introduced into an expression vector pHD313 (Dalboge et al. 1989, Gene, 79, 325–332) containing the lambda PR promoter, and optimized in ribosome binding site, and the CI ts gene in such manner that the signal peptide was fused directly to the AlaGlu-IGF-1 gene in the processing site. The obtained plasmid pHD365 was introduced into E.coli MC1061 and cultured at 28° C. for 18 hrs. Production of IGF-1 was induced by raising the temperature to 40° C.

Example 4

Extraction of AlaGlu-IGF-1 from E.coli.

To 4 liters of E.coli fermentation broth was added cysteine to a final concentration of 50 mM, and urea to a final concentration of 7M. The culture was extracted at pH 8.0 for 30 min at 6°–10° C. The extract was centrifuged for 30 min (4000 rpm) and the supernatant was either frozen or further processed immediately.

Example 5

Dialysis.

One liter of cell culture extract from Example 1 was diluted to 1.5 liters using 0.5 liters of 7M urea and 50 mM cysteine. The diluted extract was dialyzed by passing the extract through a hollow fibre apparatus (Nephros Presto, H.F. Organon). The flow was 100 ml per min. Change of buffer was carried out by reverse passing of 7M urea and 50 mM cysteine at pH 8.0 at a flow rate of 133 ml per min. The extract and buffer was recycled until an equilibrium was reached. The dialysis was terminated at ionic strength of 2.0 mS.

Example 6

Anion exchange of crude AlaGlu-IGF-1.

Figure 2:
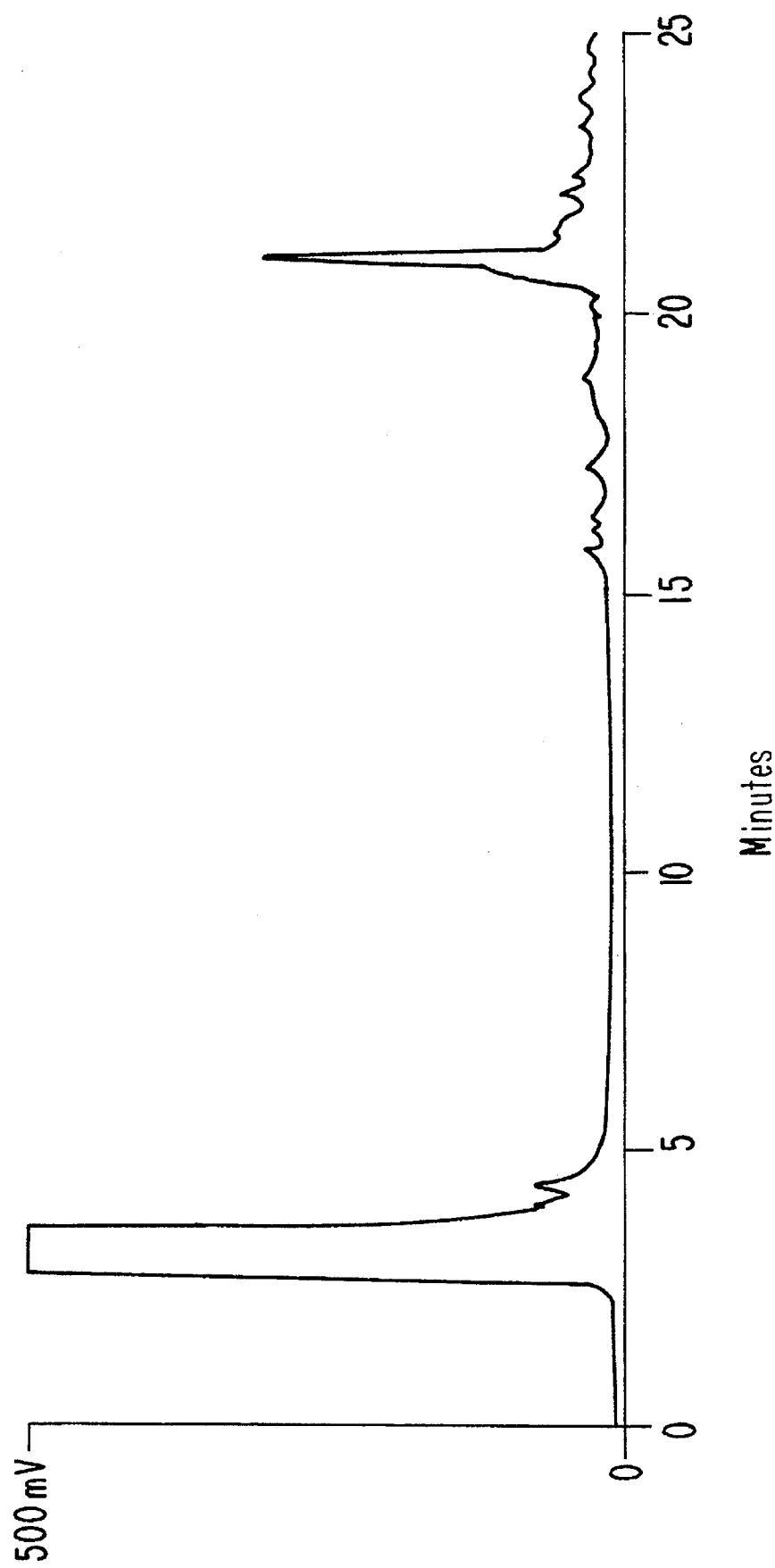
FIG. 2 shows a HPLC diagram of partly purified Ala-Glu-IGF-1 in its denatured and reduced form.

DE-52 (Whatmann) anion exchange material was equilibrated using 50 mM tris-HCl, 7M urea, 50 mM cystein at a conductivity of 2.0 mS. The equilibrated anion exchange material was mixed with the crude dialyzed extract obtained in Example 2 (protein/gel) in a ratio of 1 g to 30 ml). The crude extract was absorbed for 2 hrs at room temperature or over night at 4° C. The absorption was followed by collection of the non-absorbed proteins by filtration on Millipore A25 filter. The filtrate was reabsorbed for 3 hrs at ambient temperature on FF-Q Sepharose, which was preequilibrated using the same buffer (protein/gel ratio was 1 g/200 ml) . The quality and the quantity of the denatured AlaGlu-IGF-1 was determined by reverse phase chromatography. The column applied was a Nucleosil C4, 5 μm, 4.6×250 mm column in TFA, acetonitrile. Initial condition TFA: 0.085% in HzO (buffer A) , buffer B 0.1% TFA, 80% acetonitrile. The column was eluted using a mixture of buffer A and B and a gradient from 0–5 rain isocratic 30% B, from 5 to 25 rain linear from 30–75% B, flow: 1.0 ml/min; detection: absorption at 215 nm; ambient temperature. Denatured and reduced AlaGlu-IGF-1 is seen on FIG. 2.

Example 7

Renaturation of denatured AlaGlu-IGF-I by hollow fiber dialysis

The pooled denatured and reduced batches of AlaGlu-IGF-1 obtained as described in Example 3 was ajusted to a protein concentration of 0.2 mg/ml using 7M urea and 50 mM cystein. The pH was adjusted to 9.5 using 5M NaOH. The solution was dialyzed against a buffer consisting of 50 mM Tris-Cl, 2 mM cystein, 2 mM EDTA, pH 9.5 and 25% ethanol. The dialysis was carried out using a hollow fibre dialysis apparatus (Nephros Prosto H. F. Organon) at a flow of 100 ml/min. The dialysis buffer was exchanged when equilibrium was obtained between solution and buffer. The process was continued until a conductivity of 150 μS and a redox potential of 25 mV was reached. After the initial phase during which most of the AlaGlu-IGF-1 was folded, the solution was allowed to stabilize at 4° C. over night. 16 hrs later the reaction was terminated by adjusting the pH to 4.0 using 5M acetic acid. After dialysis, the ionic strength was 0.2 mS and the concentration of urea was estimated to be <0.05M.

Figure 3:
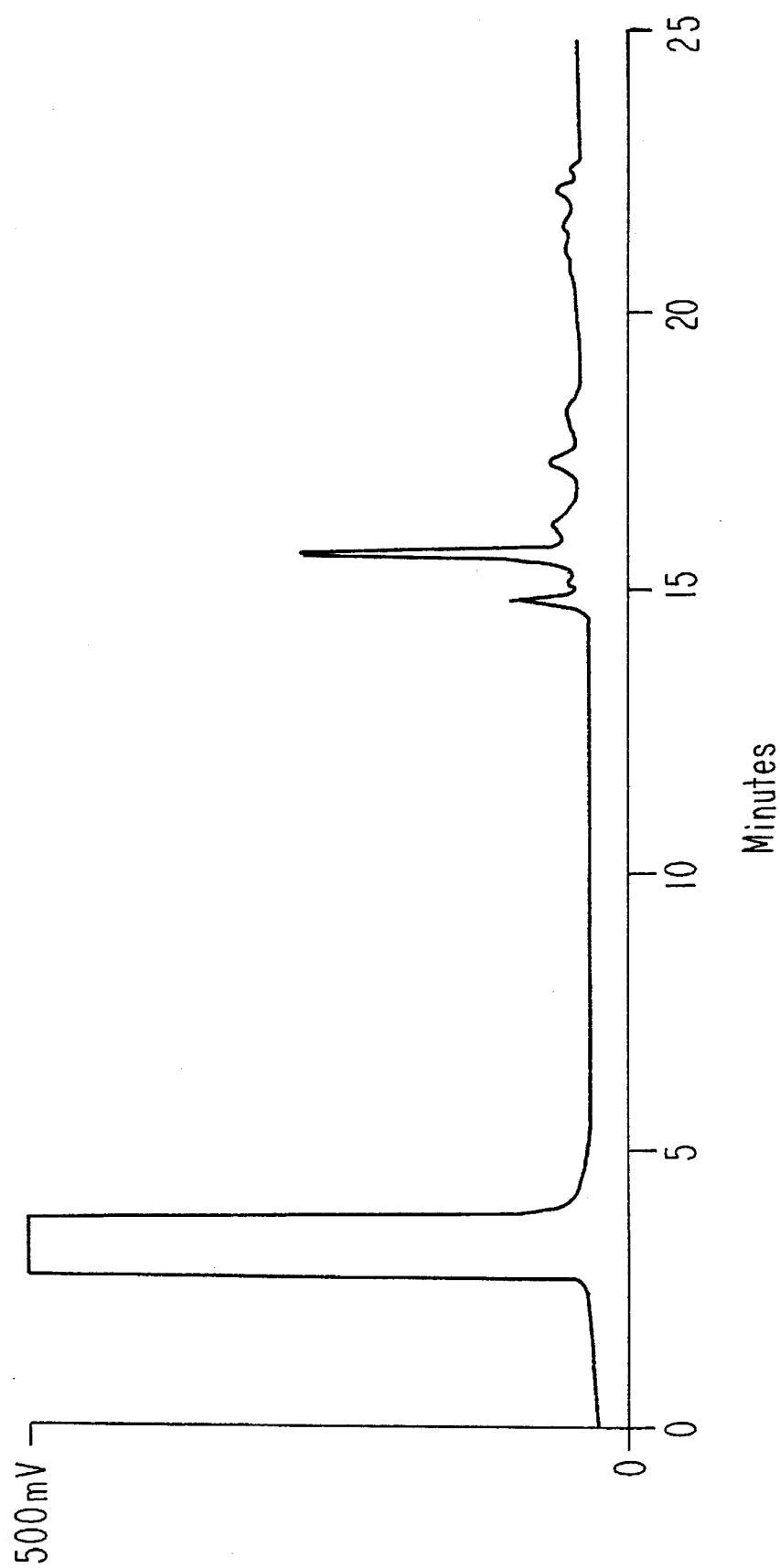
FIG. 3 shows a HPLC diagram of partly purified Ala-Glu-IGF-1 in its renatured form.
Figure 4:
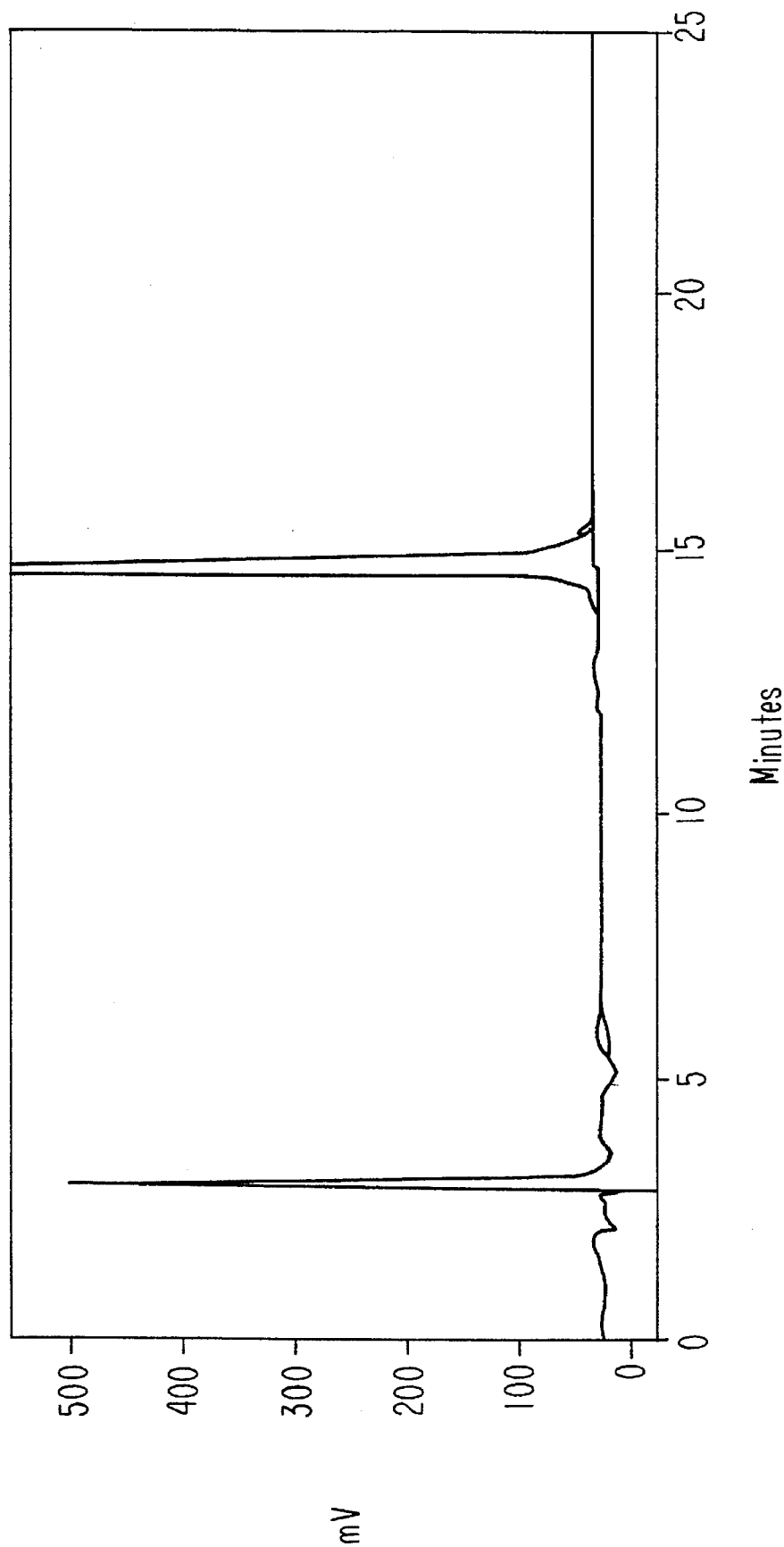
FIG. 4 shows the analytical HPLC diagram of >95% pure IGF-1.

An example of the renaturation of an aliquot of denatured and reduced AlaGlu-IGF-1 is shown in FIG. 3. The peak at RT 14.86 min. is a scrambled form of AlaGlu-IGF-1 (RT 15.68) of $M_r$ 7845 a.m.u. Peaks appearing later than AlaGlu-IGF-1 are probably scrambled forms of the molecule.

The redox electrode used for this step was ajusted using a 5 mM hydroquinone solution having a defined redox potential of 463 mV at pH 4.0.

Figure 6:
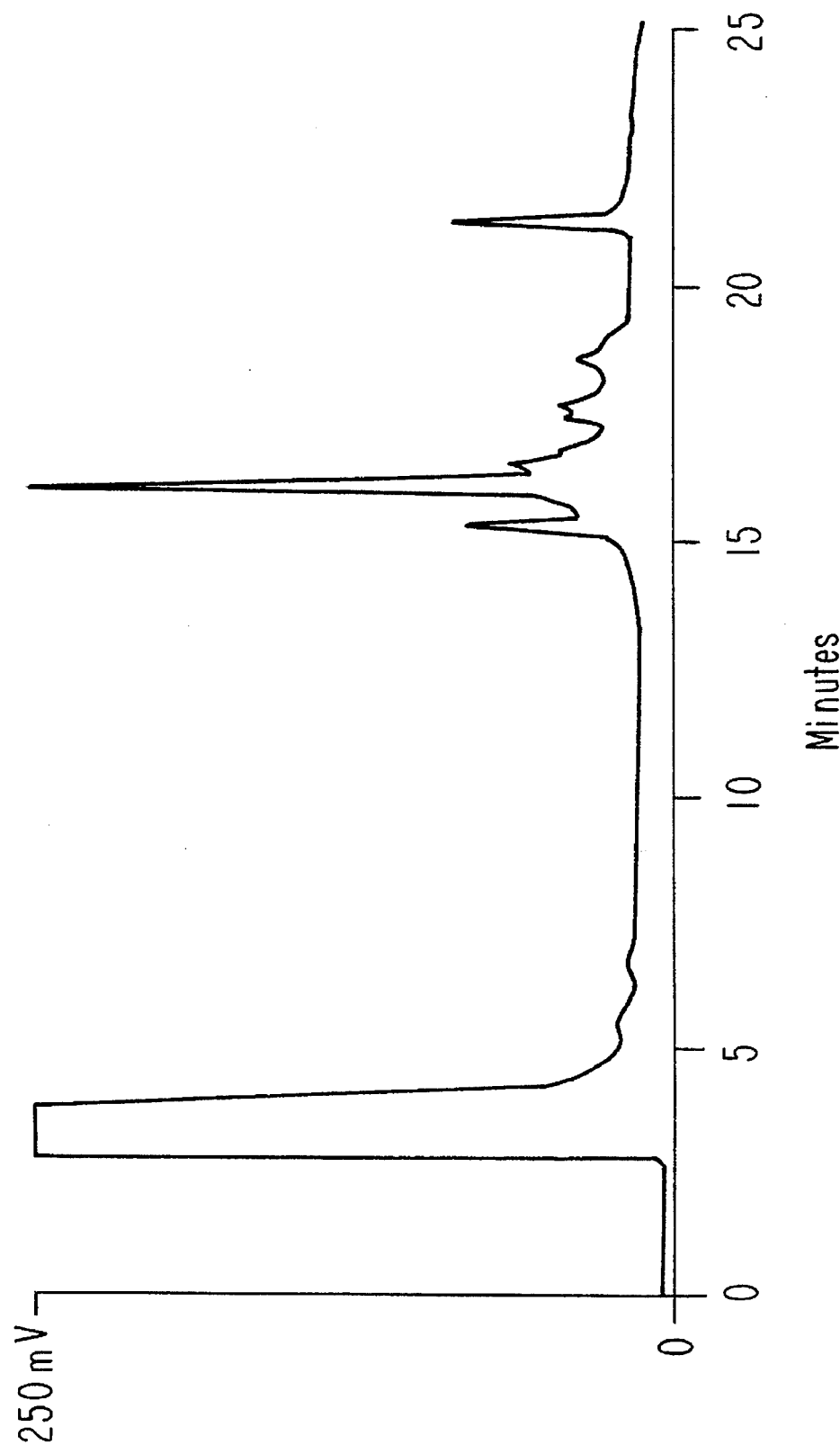
FIG. 6 shows a RP-HPLC diagram of AlaGlu-IGF-1 after renaturation by hollow fiber dialysis.

Reference is made to FIG. 6 concerning the hollow fiber RP-HPLC.

In the diagram of FIG. 6, the peak at RT 15.99 is AlaGlu-IGF-1. The peak at RT 15.21 is a scrambled form of AlaGlu-IGF-1 having a $M_r$ of 7845 a.m.u.

The renaturation of denatured AlaGlu-IGF-1 was also performed in the following three manners:

1) diluting the denatured sample, 2 mg/ml, in 50 mM Tris, 2 mM EDTA, pH 9.0, 25% ethanol to a final concentration of 0.2 mg/ml (BioRad assay) and letting the reaction proceed for 18 hours at 4° C.

2) desalting the denatured sample on an NAP 5 column (Pharmacia-LKB) in 50 mM Tris, 1 mM Cystein, 2 mM EDTA, pH 9.0, 25% Ethanol. The elution volume was 1.00 ml. The concentration of protein was 0.3 mg/ml (BioRad assay) and the reaction was allowed to procede for 18 hours at 4° C.

3) dialysis of the denatured sample (Spectapor 3.5 kD cut-off) against 50 mM Tris, 1 mM Cystein, 2 mM EDTA, pH 9.0, 25% ethanol at 4° C. for 18 hours. The initial concentration of protein was 0.3 mg/ml.

In each experiment 200 µl of the resulting solution was acidified with 30 µl of 5M acetic acid and 200 µl hereof were filtered on a Millex 0.22 µm filter and subjected to RP-HPLC analysis on a Nucleosil C4, 5 µ, 4.6×250 ntm column, Machery-Nagel 720059, A buffer: 0.085% trifluoroacetic acid (TFA), B buffer: 0.1% TFA, 80% acetonitrile using a gradient: from 0 to rain isocratic 30% B, from 5 to 25 min. linear from 30–75% B and a flow of 1.0 ml/min. detection at 215 nm at ambient temperature.

Figure 7:
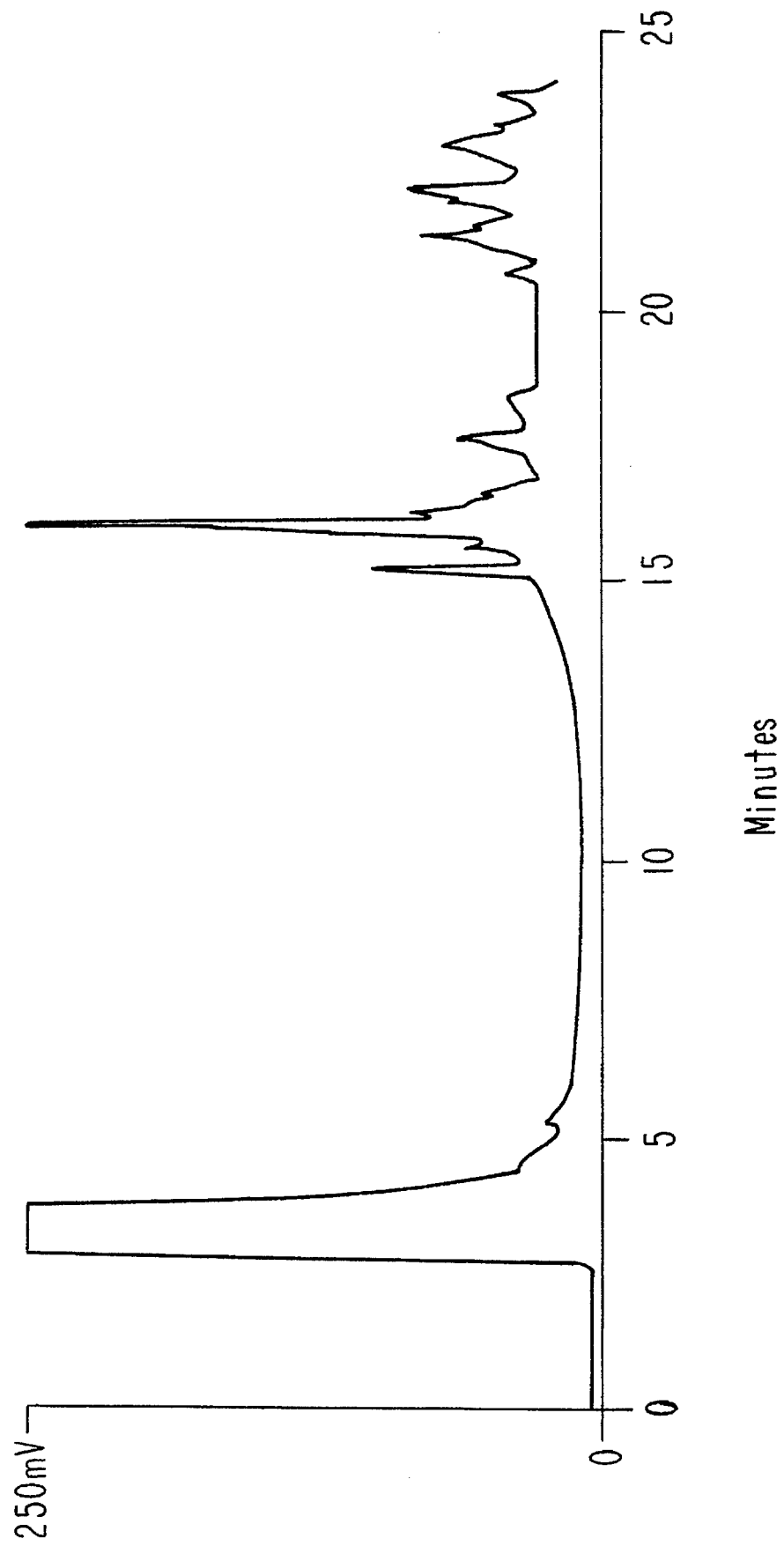
FIG. 7 shows a RP-HPLC diagram of AlaGlu-IGF-1 after renaturation by dilution.
Figure 8:
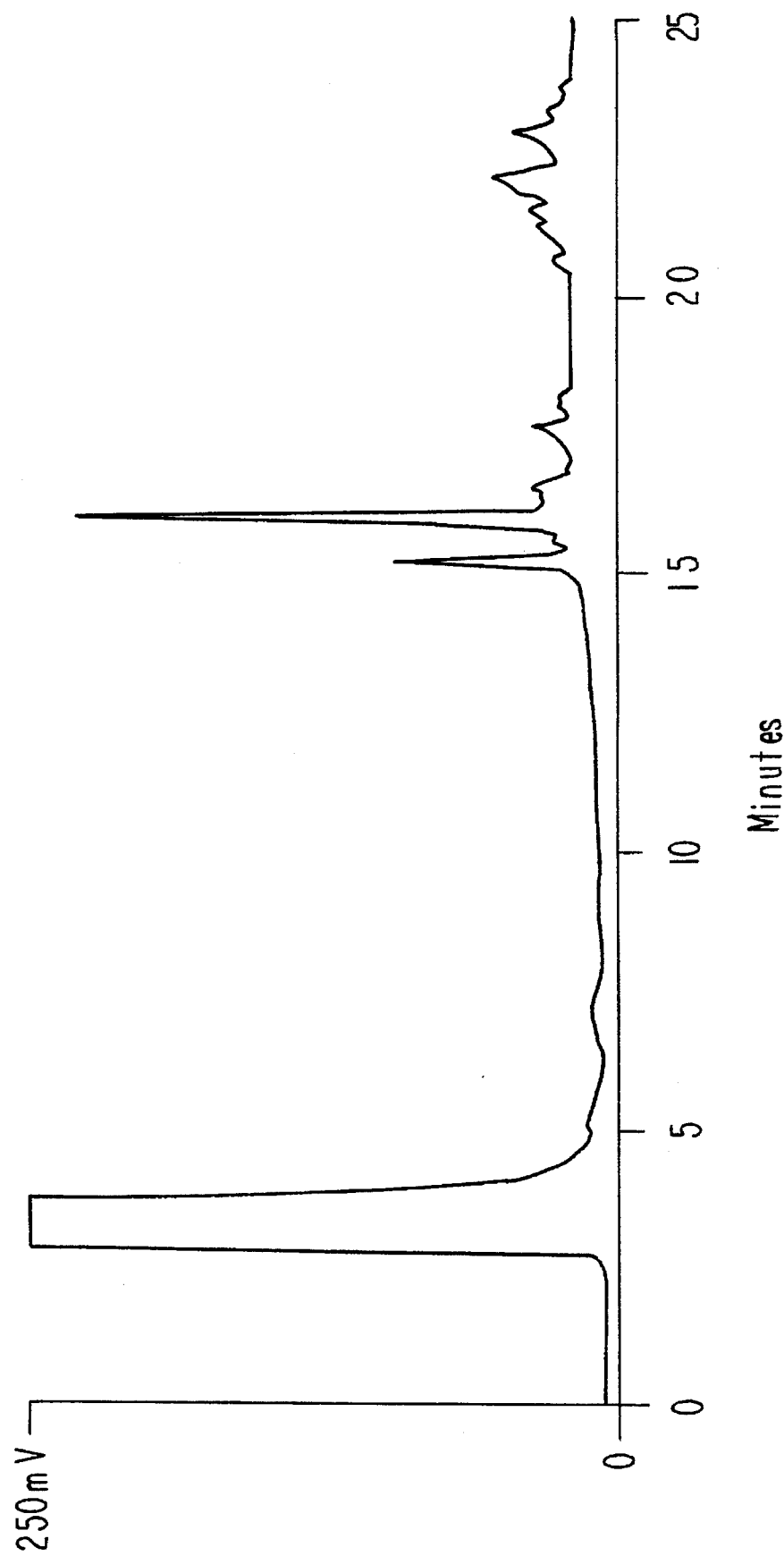
FIG. 8 shows a RP-HPLC diagram of AlaGlu-IGF-1 after renaturation by desalting.
Figure 9:
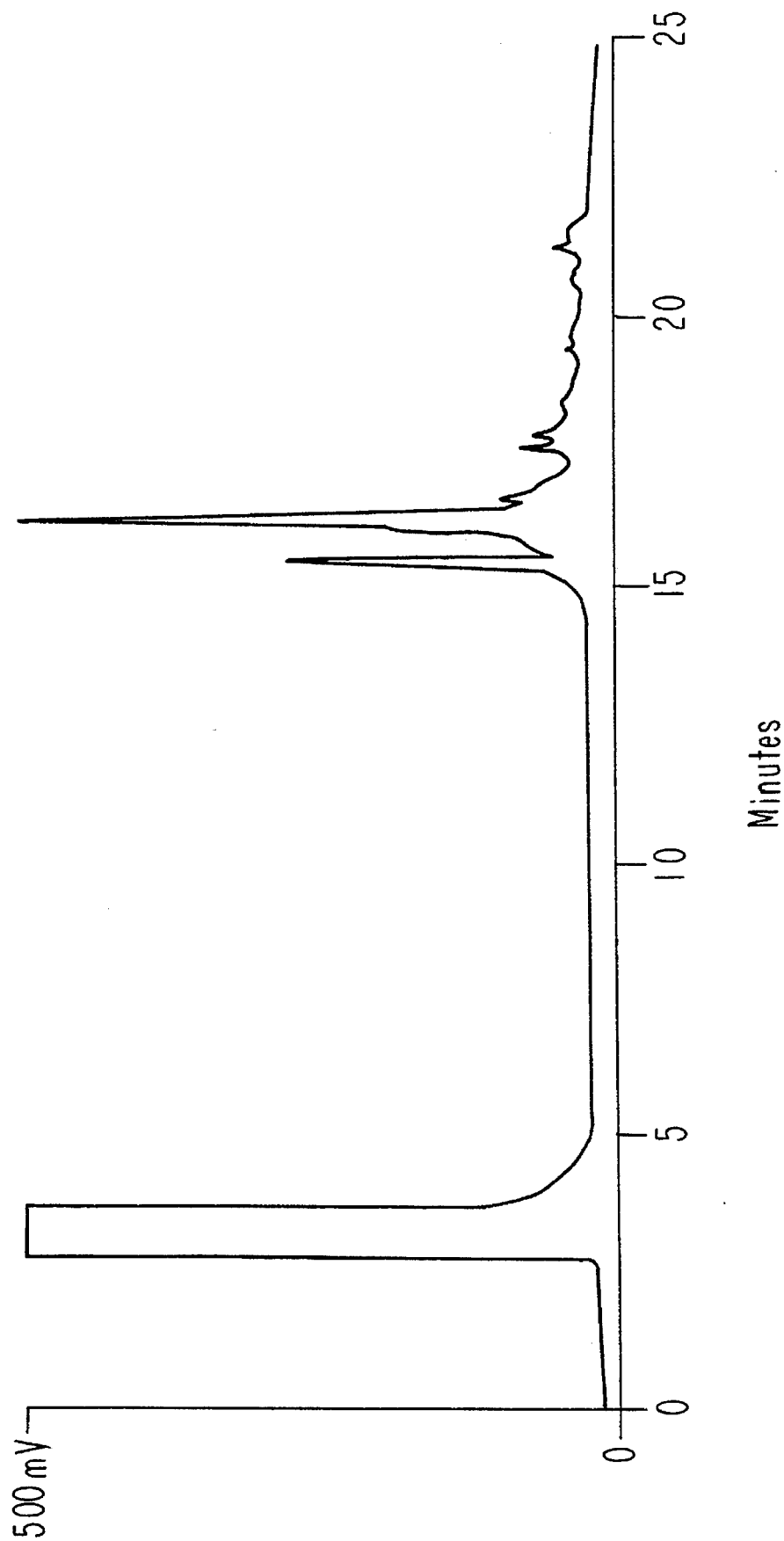
FIG. 9 shows a RP-HPLC diagram of AlaGlu-IGF-1 after renaturation by dialysis.

Reference is made to FIGS. 7–9.

In the diagram of FIG. 7, the peak at RT 16.07 min. is AlaGlu-IGF- 1. The peak at RT 15.1 is a scrambled form of AlaGlu-IGF-1 having a $M_r$ of 7845 a.m.u. Peaks appearing just later than AlaGlu-IGF-1 are probably scrambled forms as well.

In the diagram of FIG. 8, the peak at RT 16.07 is AlaGlu-IGF-1. The peak at RT 15.10 min. is a scrambled form of $M_r$ 7845 a.m.u. Peaks appearing just later than AlaGlu-IGF-1 are probably scrambled forms as well. Peaks appearing later than 20.00 min. are probably irreversibly scrambled or polymeric forms of AlaGlu-IGF-1.

In the diagram of FIG. 9, the peak at RT 16.21 min. is AlaGlu-IGF- 1. The peak at RT 15.43 min. is a scrambled form of $M_r$ 7845 a.m.u. Peaks appearing just later than AlaGlu-IGF-1 are probably scrambled forms as well.

Example 8

Cation exchange of renatured AlaGlu-IGF-1.

70 ml of FF-S Sepharose (Pharmacia-LKB) were equilibrated in 25 mM Na-phosphate, 25 mM Na-citrate adjusted with 5M NaOH to pH 4.0, 25% ethanol.

2 liters of renaturation mixture obtained as described in Example 7 were applied to the FF-S Sepharose. The suspension was gently mixed for 30 minutes at ambient temperature, and then the gel was packed in a column (3.5×20 cm²). The buffers used were A: 25 mM Na-phosphate, 25 mM Na-citrate pH 4.0, 25% ethanol B: 25 mM Na-phosphate, 25 mM Na-citrate pH 7.0, 25% ethanol both adjusted using 5M NaOH.

The flow was 0.15 ml/cmz/min, detection at 280 nm, and temperature 4° C. A gradient of 0–100% B over 60 minutes was applied. The fractions comprising AlaGlu-IGF-1 as determined by absorption at 280 nm were pooled.

Example 9

Conversion of AlaGlu-IGF-1 to IGF-1 using DAP-1.

The pool of AlaGlu-IGF-1 obtained in Example 8 was dialysed against 40 mM Na-citrate, 200 mM NaCl pH 4.0 (adjusted with 5 M NaOH) at 4° C. for 18 hours. The temperature was raised to 37° C. and 0.08 units of Catepsin C (3.4.14.1. Boehringer Mannheim) were added per mg of protein. After 30 minutes the reaction mixture was applied for a RP-HPLC column.

For termination of the reaction and purification, reaction mixture was applied to a RP-HPLC column (Novo Nordisk A/S RP18, 15µ, 10×250 mm) in 100 mM Na-phosphate buffer pH 3.0 and eluted using a step-gradient of from 30–50% ethanol over 30–60 minutes. The flow was 0.75 ml/min, detection at 280 nm, ambient temperature.

The fractions comprising IGF as determined by absorption at 280 nm were pooled.

Example 10

Cation exchange of IGF-1.

The pooled frations of IGF-1 obtained from the RP-HPLC purification as described in Example 9 was applied to a FF-S® Sepharose HR10/10 column from Pharmacia-LKB. The buffers used were A: 25 mM Na-phosphate, 25 mM Na-citrate pH 4.0, 25% ethanol B: 25 mM Na-phosphate, 25 mM Na-citrate pH 7.0, 25% ethanol both adjusted using 5M NaOH.

The flow was 0.15 ml/cm²/min, detection at 280 nm, temperature

A linear gradient of 0–100% B over 100 minutes was used. The fractions comprising IGF-1 as determined by absorption at 280 nm were pooled.

Example 11

Dialysis and gelfiltration of IGF-1.

The pooled fractions of IGF-1 obtained in Example 10 were dialyzed (Spectrapor 3.5 KD cut-off) against 0.1M acetic acid at 4° C. for 18 hours and then lyophilized. The lyophilized powder was dissolved in 7M urea to a concentration of 5 mg/ml and applied a Sephadex G50F column, (0.9×60 cm, Pharmacia-LKB) in 0.4M acetic acid. Flow was 0.2 ml/min, detection at 280 nm, temperature 4° C.

The fractions comprising IGF-1 as determined by absorption at 280 nm were pooled.

The solution obtained may be lyophilized using conventional lyophilization agents to form a stable lyophilized powder. The powder may be used for preparation of pharmaceutical preparations in a manner known per se for formulating pharmaceutical preparations comprising IGF-1.

We claim:

1. A method for the renaturation of AlaGlu-IGF-1 wherein AlaGlu-IGF-1, in a denatured and reduced form, is folded during changing the redox potential from −40 mV to +20 to +40 mV by dialysis against a buffer containing from 20–40% v/v ethanol over a period of up to 5 hours at a protein concentration of 0.1 to 0.6 mg/ml and a conductivity of 0.15 to 0.3 mS, at ambient temperature and a pH of from 7.5 to 10.0 and finally acidifying the mixture to a pH below 5.

2. A method for producing human IGF-1 comprising (i) expressing AlaLGlu-IGF-1 in a microorganism transformed with an expression vector comprising an inducible promoter coupled directly to the DNA coding for human Ala-Glu-IGF-1 and a signal sequence providing for secretion of the expressed AlaLGlu-IGF-1, (ii) extracting the expressed human AlaLGlu-IGF- 1 at a pH of more than 6.0 using urea in the presence of a reducing agent to obtain an extract, (iii) subjecting the extract of step (ii) to chromatography on an anion exchange gel selected from the group consisting of DEAE, DE and FF-Q' in a buffer comprising urea and a reducing agent adjusted to 1.8–2.2 mS and pH 7.8–8.2 to obtain an isolated human Ala-Glu-IGF-1 solution, (iv) renaturing the isolated human Ala-Glu-IGF-1 of step (iii) comprising changing the redox potential of the isolated human Ala-Glu-IGF-1 solution from a negative to a positive value by dialysis against a buffer containing an alcohol at a protein concentration from 0.1 to 0.6 mg/ml at ambient temperature and a pH of from 7.5 to 10.0 and finally acidifying the mixture to a pH below 5 to obtain renatured human Ala-Glu-IGF-1, (v) cleaving the Ala-Glu extension from the renatured human Ala-Glu-IGF-1 of step (iv) with dipeptidyl amino peptidase to obtain renatured human IGF-1, (vi) isolating the renatured human IGF-1 of step (v) using reversed-phase high pressure liquid chromatography and cation exchange chromatography, and (vii) gel filtrating and lyophilizing the isolated human IGF-1 of step (vi).

3. A method as claimed in claim 2 wherein the microorganism is *E.Coli*.

4. A method as claimed in claim 2 wherein the promoter is a temperature sensitive promoter selected from the group consisting of $\lambda_{P_r}$, $\lambda_{PL}$, $\lambda_{P_{R'}}$, and the signal sequence is selected from the groups consisting of LamB, OmpA or OmpF.

5. A method as claimed in claim 4 wherein promoter is the $\lambda_{P_r}$ and the signal sequence is the OmpA-sequence.

6. A method as claimed in claim 2 wherein the extraction of AlaGlu-IGF-1 in step ii is carried out using a buffer having a concentration of urea greater than 4M.

7. A method as claimed in claim 2 wherein the extraction of AlaGlu-IGF-1 in step ii) is carried out using a buffer comprising 7M urea, 50 mM Cys and pH 8.0.

8. A method as claimed in claim 2 wherein the chromatography of the extract from step iii) is carried out at a conductivity of 2.0 mS at pH 8.0.

9. A method as claimed in claim 2 wherein the chromatography of the extract from step iii) is carried out as batch chromatography on DE and repeated on FF-Q®.

10. A method as claimed in claim 2 wherein the renaturation of AlaGlu-IGF-1 in step IV is carried out at a conductivity of 0.2 mS.

11. A method as claimed in claims 2 wherein the renaturation of step iv) is carried out changing the redox potential linearly from about −40 mV to +25 to +30 mV over a period of 3 hours.

12. A method as claimed in claim 2 wherein the renaturation of step iv) is carried out at a conductivity of 0.2 mS, a concentration of proteins of 0.2 mg/ml, and a pH from 8.5 to 9.5.

13. The method of claim 12 in which the renaturation of step iv) is carried out at a pH from 8.5 to 9.0.

14. A method as claimed in claim 2 wherein the renaturation of step iv) is carried out at a temperature of from 20° to 22° C.

15. A method as claimed in claim 2 wherein the renaturation of step iv) is carried out passing the AlaGlu-IGF-1 through a hollow fiber device at a flow rate of from 25 to 250 ml/min.

16. The method of claim 15 in which the flow rate is about 100 ml/min.

17. A method as claimed in claim 2 wherein the acidification of step iv) is carried out by adding 5M acetic acid.

18. A method as claimed in claim 2 wherein the cleaving of step v) is carried out using DAP-I in a concentration of 0.08 units DAP-I per mg of protein in the presence of NaCl, adjusting the protein concentration to approximately 1 mg/ml in a 40 mM acetate buffer at pH 4.0 and at 37° C.

19. The method of claim 2 in which human AlaGlu-IGF-1 is extracted in the presence of a chelating agent.

20. The method of claim 2 in which the isolated human Ala-Glu-IGF-1 solution is dialyzed over a period of up to 5 hours at a conductivity of 0.15–0.3 mS and in which the alcohol is ethanol in a concentration from 20 to 40% (v/v).

* * * * *